(12) United States Patent
Lee et al.

(10) Patent No.: US 6,989,251 B2
(45) Date of Patent: Jan. 24, 2006

(54) METHOD FOR MANUFACTURING HIGHLY-CONCENTRATED POLYGLUTAMIC ACID WITH ADDITIONAL SUPPLY OF SACCHARIDES

(75) Inventors: Sang-Yup Lee, Taejon (KR); Ho-Nam Chang, Taejon (KR); Nagendra Narayan Thakur, Taejon (KR); Jin-Hwan Do, Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 473 days.

(21) Appl. No.: 10/300,711

(22) Filed: Nov. 19, 2002

(65) Prior Publication Data

US 2003/0124674 A1 Jul. 3, 2003

Related U.S. Application Data

(63) Continuation of application No. PCT/KR00/00761, filed on Jul. 14, 2000.

(30) Foreign Application Priority Data

May 20, 2000 (KR) ............................... 2000-27278
Nov. 29, 2001 (WO) ................................. 01/90395

(51) Int. Cl.
*C12P 21/04* (2006.01)
*C12P 13/14* (2006.01)

(52) U.S. Cl. .................... 435/106; 435/71.1; 435/71.2; 435/110

(58) Field of Classification Search ............... 435/71.1, 435/71.2, 106, 110, 836
See application file for complete search history.

(56) References Cited

U.S. PATENT DOCUMENTS

5,268,279 A * 12/1993 Kanegae et al. ........... 435/71.2

OTHER PUBLICATIONS

Jin Hwan Do et al., Efficient Recovery of γ-Poly (Glutamic Acid) from Highly Viscous Culture Broth, Biotechnology and bioengineering, 76:219-223 (2001).

Ing-Lung Shih et al., The Production of Poly- (γ-Glutamic Acid) from Microorganisms and its Various Applications, Bioresource Technology, 79:207-225 (2001).

Jin Hwan Do et al., Effect of Impeller Clearance on Flow Structure and Mixing in Bioreactor with Two-Stage Impellers, Eng. Life Sci., 5:181-185 (2001).

Mr. Ashiuchi et al., Biochemistry and Molecular Genetics of Poly-γ-Glutamate Synthesis, Appl. Microbiol. Biotechnol., 59:9-14 (2002).

M. Ashiuchi et al., Isolation of *Bacillus subtilis* (Chungkiikjang), a Poly-γ-Glutamate Procuder with High Genetic Competence, Appl. Microbiol. Biotechnol., 57:764-769 (2001).

Sung Ho Yoon et al., Production of Poly-γ-Glutamic Acid by Fed-vatch Culture of *Bacillus licheniformis*, Biotechnology Letters, 22:585-588 (2000).

Makoto Ashiuch et al., Properties of Glutamate Racemase from *Bacillus subtilis* IFO 3336 Producing Poly-γ-Glutamate, J. Biochem., 123:1156-1163 (1998).

Gregory A. Birrer et al., γ-Poly (Glutamic Acid) Formation by *Bacillus licheniformis* 9945a: Physiological and Biochemical Studies, Int. J. Biol.Macromol., 16:265-275 (1994).

Yoshihiro Ogawa et al., Efficient Production of γ-Polyglutmic Acid by *Bacillus subtilis* (natto) in Jar fermenters, Biosci. Biotech. Biochem., 61:1684-1687 (1997).

Frederic A. Troy, Chemistry and Biosynthesis of the Poly (γ-D-Glutamyl) Capsule in *Bacillus licheniformis*, The Journal of Biological Chemistry, 248:305-315, 316-324 (1973).

M. Kunloka, Biosynthesis of the Poly (γ-Glutamic Acid) from L-Glutamine, Citric Acid and Ammonium Sulfate in *Bacillus subtilis* IFO3335, Appl. Microbiol. Biotechnol., 44:501-506 (1995).

* cited by examiner

*Primary Examiner*—Herbert J. Lilling
(74) *Attorney, Agent, or Firm*—Knobbe Martens Olson & Bear LLP

(57) ABSTRACT

The present invention provides a method for manufacturing highly-concentrated polyglutamic acid by culturing an aerobic micro-organism of *Bascillus* sp. with the additional supply of saccharides. The method for manufacturing polyglutamic acid comprises a step of culturing *Bascillus* sp. in a fed-batch or batch culture while supplying saccharides to the culture. Since the method for manufacturing highly-concentrated polyglutamic acid can be applicable to the industrial scale fermentation, mass production of polyglutamic acid can be feasible in a cost-efficient way.

20 Claims, 3 Drawing Sheets

METHOD FOR MANUFACTURING HIGHLY-CONCENTRATED POLYGLUTAMIC ACID WITH ADDITIONAL SUPPLY OF SACCHARIDES

RELATED APPLICATIONS

This application is a continuation under 35 U.S.C. § 365 (c) claiming the benefit of the filing date of PCT Application No. PCT/KR00/00761 designating the United States, filed Jul. 14, 2000. The PCT Application was published in English as WO 01/90395 A1 on Nov. 29, 2001, and claims the benefit of the earlier filing date of Korean Patent Application No. 2000-27278, filed May 20, 2000. The PCT publication WO 01/90395 A1 and Korean Patent Application No. 2000-27278 are incorporated herein by reference in their entirety.

BACKGROUND OF THE INVENTION

1. Field of the Invention

The present invention relates to a method for manufacturing highly-concentrated polyglutamic acid with the additional supply of saccharides, more specifically, to a method for manufacturing highly-concentrated polyglutamic acid with high yield, but without formation of undesirable side-products by culturing a microorganism of Bacillus sp. under a fed-batch or batch condition while saccharides are additionally supplied to the culture.

2. Description of the Related Technology

Polyglutamic acid produced by microorganism is completely biodegradable, thus, has been used as an ingredient of foods and cosmetics. Recently, researches on utilization of polyglutamic acid as medical material (see: Kishida, A. and Murakami, K. et al., J. Bioactive and Compatible Polymers, 13:271–278, 1998), functional carrier, membrane material, and electrical material are being actively undertaken in the art (see: U.S. Pat. No. 5,693,751). In line with the continued efforts to produce highly-concentrated polyglutamic acid, there have been reports on a medium composition optimized for flask or batch fermentation (see: Ko, Y. K. and Gross, R. A., Biotechnol. Bioeng., 57:430–437, 1998) and an effective medium supplemented with citrate for fed-batch fermentation (see: Korean Patent No. 250627), which are, however, proven to be less satisfactory in a sense that glycerol and citrate contained in the medium cannot be utilized readily as an energy source by the microorganism. Nonetheless, there is no teaching on a medium supplemented with efficient sacchrides such as glucose or fructose for the fed-batch fermentation. Since saccharides produce a good deal of ATP through the metabolic pathway of microorganisms, they are good energy sources for the process consuming a lot of ATP such as synthetic pathway of polyglutamic acid (see: Troy F. A., J. Biol. Chem., 248: 305–315, 1973).

Therefore, there is a continuing need to develop fermentation techniques to increase yield of polyglutamic acid by the efficient supply of saccharides readily available to microorganisms.

SUMMARY OF THE INVENTION

The present inventors have made an effort to establish a fermentation technique by which highly-concentrated polyglutamic acid can be produced with high yield, thus, they have found that highly-concentrated polyglutamic acid can be obtained with high yield but without formation of undesirable side-products by culturing a microorganism of Bacillus sp. under a fed-batch or batch condition while saccharides are additionally supplied to a medium containing glycerol, citric acid and glutamic acid.

A primary object of the present invention is, therefore, to provide a method for manufacturing highly-concentrated polyglutamic acid with the additional supply of saccharides.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

Figure 1:
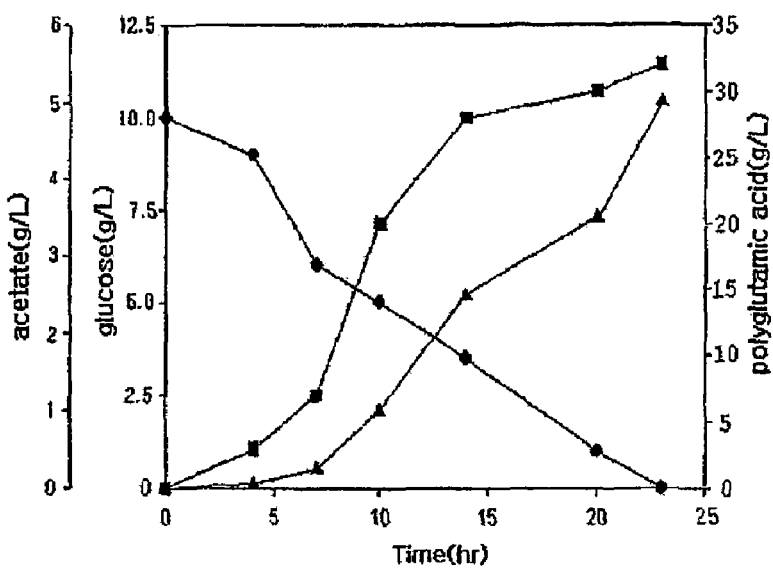
FIG. 1 is a graph showing the time course of polyglutamic acid production in a batch fermentation process with the additional supply of saccharide.

The method for manufacturing highly-concentrated polyglutamic acid by culturing a microorganism of Bacillus sp. with the additional supply of saccharides is characterized by comprising a step of additional supply of saccharide to a medium containing glycerol, citric acid and glutamic acid to maintain the concentration of saccharide at a range of 2 to 10 g/L: The microorganism of Bacillus sp. is preferably, but not limited to, Bacillus licheniformis (ATCC 9945A), and the fermentation process may include batch fermentation or fed-batch fermentation, preferably fed-batch fermentation. When the fermentation is performed under a batch condition, the saccharide concentration is controlled preferably at 2 to 10 g/L, and under a fed-batch condition, preferably at 2 to 3 g/L by adding saccharide additionally. The saccharide includes monosaccharide or disaccharide such as fructose, lactose, glucose, sucrose, maltose or galactose, most preferably glucose.

Under a previous knowledge that a lot of ATP is consumed for a microorganism to synthesize polyglutamic acid, the present inventors have made an effort to improve the production yield and production rate via additional supply of saccharide which can be readily utilized by a microorganism as an energy source.

First, to examine the effect of saccharides on polyglutamic acid production, various types of saccharides at various concentrations were added to the fermentation under a batch condition, and subsequent synthesis of polyglutamic acid and formation of side-products such as polysaccharides were investigated. It has been found in this experiment that the yield of polyglutamic acid can be increased by supplying additional saccharides, but formation of undesirble side-products such as polysaccharides was also detected above a certain concentration of saccharides. Since side-products cause many problems in isolation and purification of polyglutamic acid, and even a very small quantity of side-products in a small scale fermentation may cause serious problems when it comes to a large scale fermentation, it is very important to maintain saccharide concentration as low as possible not to form undesirable side-products. Although the concentration of saccharides was kept at a concentration low enough not to form side-products, the yield of polyglutamic acid was decreased due to the slowed growth rate of microorganism caused by acetic acid accumulated after a certain period of time, thus, it has been found that preferable is employing fed-batch fermentation in which the low concentration of saccharides can be kept constant throughout the fermentation.

The conventional fed-batch fermentation to produce polyglutamic acid is made by culturing a microorganism in a citrate-free medium followed by adding citrate after the growth of microorganism reached at certain stage, or concentrated E medium was added while the concentration of citrate kept low. In the present invention, the improvements on the production yield and production rate were accomplished by overcoming the shortage of energy source available, thus, the microorganism was grown under a fed-batch condition with a constant saccharide concentration obtained by additional supply of saccharide. As shown in the batch fermentation above, the best result was obtained with glucose, thus, glucose was used as an energy source and was supplied at a low concentration to avoid formation of side-products and excessive acetic acid. As a result, the yield of polyglutamic acid by the fed-batch fermentation was increased substantially when compared with that of the conventional batch fermentation.

The present invention is further illustrated in the following examples, which should not be taken to limit the scope of the invention.

EXAMPLE 1

Effect of Saccharides on Batch Fermentation Process

In order to measure the concentration of polyglutamic acid and identify the polysaccharides formed in culture, *Bacillus licheniformis* (ATCC 9945A) was cultured in 50 mL of E medium supplemented with various concentrations of various saccharides in a 250 mL flask under a condition of 250 rpm and 37° C. for 60 hours and then concentration of polyglutamic acid produced was measured and types of polysacchrides produced were identified (see: Table 1). Composition of E medium is as follows: 80 g/L glycerol, 20 g/L L-glutamic acid, 12 g/L citric acid, 7 g/L $NH_4Cl$, 0.5 g/L $K_2HPO_4$, 0.5 g/L $MgSO_4$ $7H_2O$, 0.04 g/L $FeCl_3$ $6H_2O$, 0.15 g/L $CaCl_2$ $2H_2O$ and 0.104 g/L $MnSO_4H_2O$.

TABLE 1

Identification of polysaccharides formed at various concentrations of saccharides

| Concentration of supplied saccharide (unit: g/L) | Concentrations of polyglutamic acid produced depending on supplied saccharide (unit: g/L) | | | | | |
|---|---|---|---|---|---|---|
| | fructose | lactose | glucose | sucrose | maltose | galactose |
| 5  | 20(x)* | 13(x) | 21(x)   | 17(x) | 5(x)  | 21(x) |
| 10 | 17(x)  | 14(x) | 24(x)   | 20(x) | 7(x)  | 19(x) |
| 20 | 19(o)  | 6(x)  | 22(o)   | 23(o) | 14(x) | 17(x) |
| 40 | 15(o)  | 8(o)  | 29.2(o) | 26(o) | 20(o) | 15(o) |

*( ) represents whether polysaccharides were formed or not, where o represents the existence of polysaccharide and x represents the absence, respectively.

As shown in Table 1 above, when the concentrations of saccharides were 40 g/L or higher, formation of polysaccharide side-products was detected in all samples regardless of the type of saccharide added. When glucose concentration was maintained at 10 g/L or lower, 24 g/L polyglutamic acid was produced without formation of polysaccharide side-products, which is 1.6 fold higher than 15 g/L of polyglutamic acid concentration obtained using E medium. From the results above, it has been found that the concentration of supplied saccharide should not exceed 10 g/L to improve the yield of polyglutamic acid by inhibiting formation of side-products although it may vary depending on the types of saccharide. Accordingly, it was clearly demonstrated that the productivity of polyglutamic acid can be increased by using a carbon source of saccharides at an optimum concentration.

EXAMPLE 2

Batch Fermentation with Additional Supply of Glucose

Since the formation of side-product decreased substantially when the concentration of saccharides was kept at or lower than 10 g/L, *Bacillus licheniformis* (ATCC 9945A) was grown in E medium supplemented with 10 g/L glucose under a batch fermentation condition. The fermentation was carried out in 3 L of E medium in a 5 L fermenter under a condition of pH 6.5, 37° C. and dissolved oxygen tension was kept above 10% air saturation by flowing a mixture of pure oxygen and air (see: FIG. 1). FIG. 1 is a graph showing the time course of polyglutamic acid production in a batch fermentation process with the additional supply of saccharide; (●) indicates concentration of glucose, (▲) indicates concentration of acetate, and (■) indicates concentration of polyglutamic acid, respectively. As shown in FIG. 1, 32 g/L polyglutamic acid was obtained but no side-product was formed after 23 hour-fermentation, and concentration of acetate in the medium was increased with culture time, resulting in rapid decrease in growth rate of cells and subsequent decrease in productivity of polyglutamic acid.

EXAMPLE 3

Fed-Batch Fermentation

Figure 2:
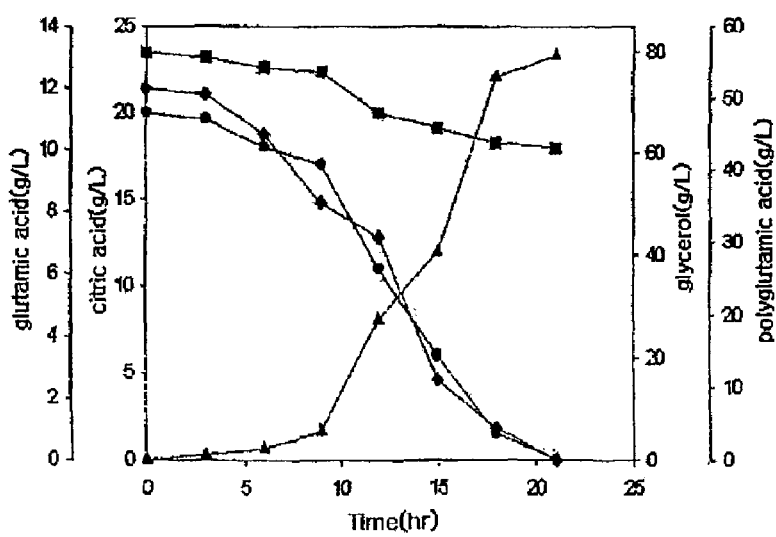
FIG. 2 is a graph showing the time course of polyglutamic acid production in a fed-batch fermentation process with the additional supply of saccharide.

Under an assumption that the yield of polyglutamic acid can be increased by inhibiting formation of acetate as shown in Example 2, the fed-batch fermentation which maintains constant concentration of saccharides, was carried out. For production of polyglutamic acid, fed-batch process is an efficient fermentation process in which yield and concentration can be increased in parallel by supplying substrates properly. Thus, a representative saccharide, glucose, was employed to fed-batch fermentation to increase productivity and concentration of polyglutamic acid. Same culture condition was employed as in Example 2 except for addition of glucose (see: FIG. 2). Glucose was added at the early stage of logarithmic phase of growth, and concentration of glucose in the culture was maintained at 3 g/L. As a result, acetate was not detected after 20 hour-fermentation contrary to the batch fermentation in Example 2. FIG. 2 is a graph showing a fed-batch fermentation of polyglutamic acid where the glucose concentration was maintained at 3 g/L; (●) indicates concentration of glutamic acid, (▲) indicates concentration of polyglutamic acid, (♦) indicates concentration of citric acid, and (■) indicates concentration of glycerol, respectively. As shown in FIG. 2, 57.5 g/L polyglutamic acid was obtained after 22 hour-fermentation, 2.6 g/L per hour, which is two fold increase in productivity compared to the conventional process, and it has been found that uptake of glycerol, citrate or glutamic acid by the microorganism was not affected by the addition of glucose. Since it has been known that uptake of glycerol, citrate or glutamic acid from the medium by the microorganism is an essential step for the production of polyglutamic acid (see: Korean Patent No. 250627), it can be stated that the addition of glucose as an energy source did not exert catabolic repression by inhibiting the microorganism from uptaking of glycerol, citric acid or glutamic acid which may result in decrease in polyglutamic acid production.

COMPARATIVE EXAMPLE 1

Batch Fermentation

Figure 3:
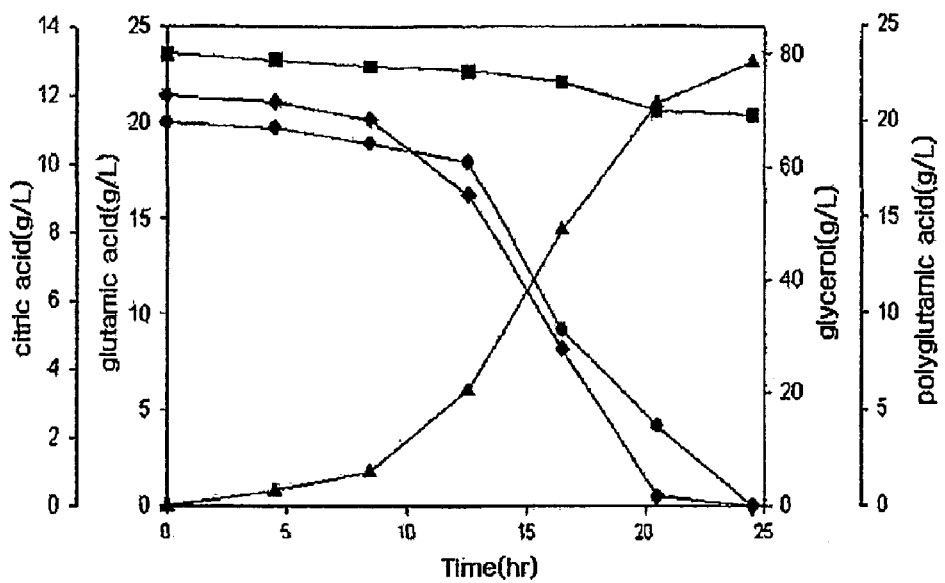
FIG. 3 is a graph showing the time course of polyglutamic acid production in a batch fermentation process.

To verify the method for manufacturing polyglutamic acid of the invention is superior to the conventional methods, Bacillus licheniformis (ATCC 9945A) was grown in E medium under the same batch fermentation condition as described in Example 3 except for the addition of saccharide (see: FIG. 3). FIG. 3 is a graph showing the time course of polyglutamic acid production in a batch fermentation: (●) indicates concentration of glutamic acid, (▲) indicates concentration of polyglutamic acid, (♦) indicates concentration of citric acid, and (■) indicates concentration of glycerol, respectively, wherein 23.5 g/L polyglutamic acid was obtained after 22 hour-fermentation.

Figure 4:
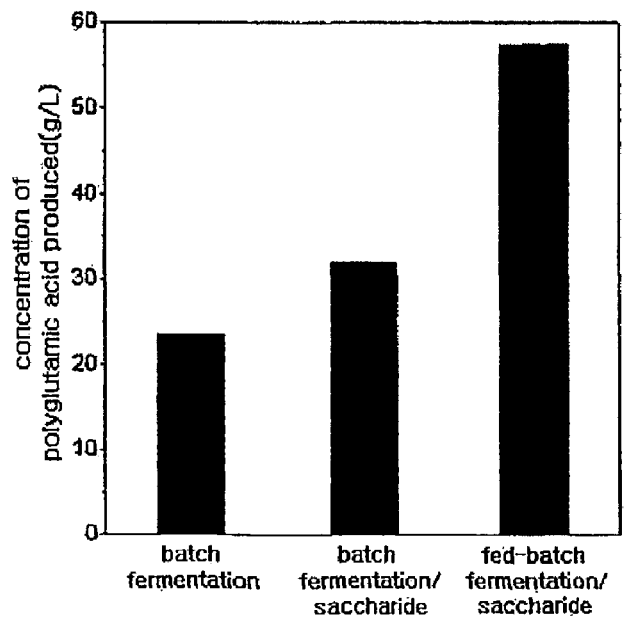
FIG. 4 is a graph showing the comparison of concentrations of polyglutamic acid produced by various fermentation processes.

Comparing the results of Examples 2 and 3 and Comparative Example 1, it has been found that the yield of polyglutamic acid by batch fermentation with the additional supply of saccharide was higher than that without the additional supply of saccharide as in conventional method, and when saccharide was supplied additionally, fed-batch fermentation yield higher productivity of polyglutamic acid than batch fermentation (see: FIG. 4).

EXAMPLE 4

A Large Scale Fed-Batch Fermentation

Figure 5:
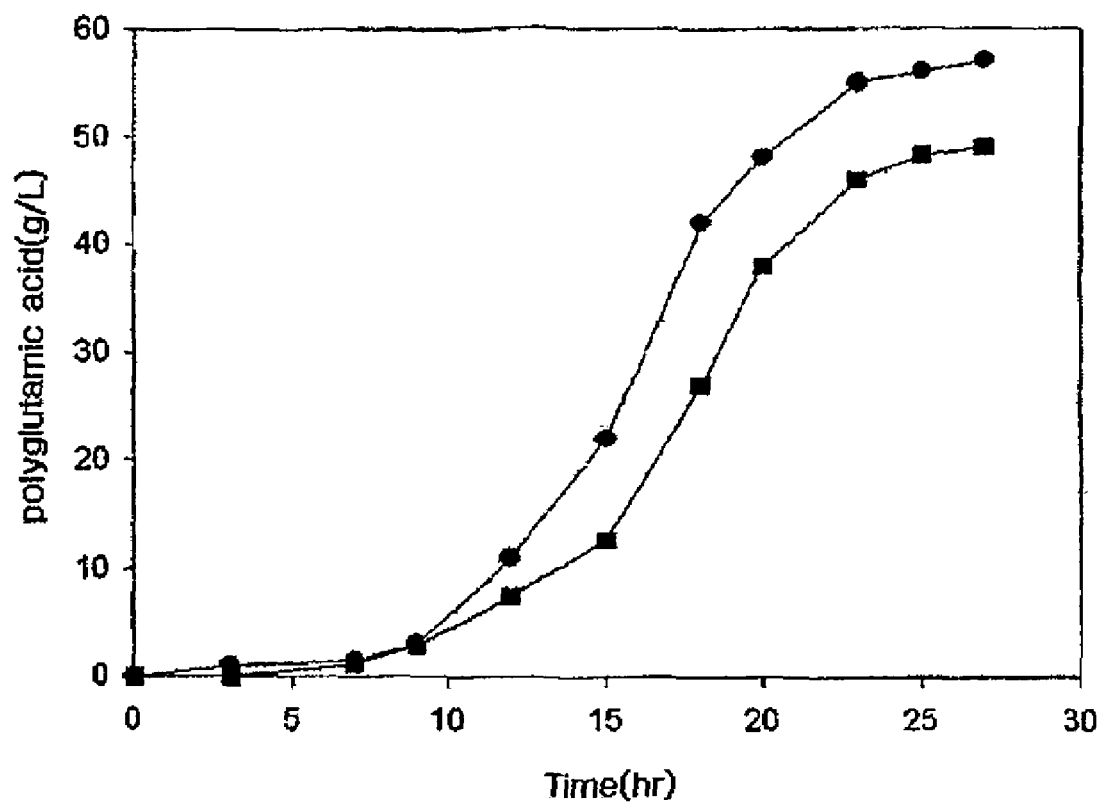
FIG. 5 is a graph showing the time course of polyglutamic acid production in a large scale fed-batch fermentation process.

To examine whether the process disclosed in Example 3 can be applied to a large scale fermentation of polyglutamic acid, fed-batch fermentations with the additional supply of glucose as in Example 3 were carried out in a 30 L fermenter and in a 300 L fermenter, respectively. Twenty liter of E medium was added into a 30 L fermenter and 200 L of E medium was added into a 300 L fermenter, and the dissolved oxygen tension in a 300 L fermenter was controlled at 5 to 10% air saturation by applying a pressure of 0.1 to 0.4 atm instead of using pure oxygen. After 22 hour fermentation, 55 g/L and 46 g/L polyglutamic acid were obtained from 30 L and 300 L fermenter, respectively (see: FIG. 5). FIG. 5 is a graph showing the time course of polyglutamic acid production in a large scale fed-batch fermentation process: (●) indicates 30 L fermenter and (■) indicates 300 L fermenter. As shown in FIG. 5, the result obtained from 30 L fermenter was similar to that from 5 L fermenter, but the concentration and yield of polyglutamic acid from 300 L fermenter was turned out to be a little lower, which is speculated to be attributable to non-homogeneous mixing and low rate of mass transfer caused by high viscosity of the culture broth. Therefore, it can be expected that the large scale fermention would produce similar results to the small scale fermentation if the problems posed above could be overcome by optimal design of the fermenter. The polyglutamic acid concentrations of 55 g/L and 46 g/L are higher than those obtained by conventional methods, thus, the process stated in Example 3 was found to be applicable to a large scale fermentation. It will be well understood in the art that the above strategy can be applicable especially to microorganisms of Bacillus sp. producing polyglutamic acid.

As illustrated and demonstrated above, the present invention provides a method for manufacturing highly-concentrated polyglutamic acid with high yield, but without formation of undesirable side-products by culturing a microorganism of Bacillus sp. under a fed-batch or batch condition while readily usable saccharides are additionally supplied to the culture. Since the method for manufacturing highly-concentrated polyglutamic acid can be applicable to the industrial scale fermentation, mass production of polyglutamic acid can be feasible in a cost-efficient way.

What is claimed is:

1. A method of producing polyglutamic acid, comprising:
culturing a microorganism of Bacillus sp. in a culture medium comprising a saccharide at a concentration to produce polyglutamic acid; and
adding a saccharide to the culture medium to maintain the concentration from about 2 to about 10 g/L.

2. The method of claim 1, wherein the microorganism of Bacillus sp. is Bacillus licheniformis (ATCC 9945A).

3. The method of claim 1, wherein the saccharide is one or more selected from the group consisting of fructose, lactose, glucose, sucrose, maltose and galactose.

4. The method of claim 1, wherein the culture medium further comprises one or more selected from the group consisting of glycerol, citric acid and glutamic acid.

5. The method of claim 1, further comprising collecting polyglutamic acid.

6. The method of claim 1, wherein the method is carried out in a batch mode except that the saccharide is added to the culture medium during the culturing.

7. The method of claim 1, wherein the saccharide is continuously added to the culture medium.

8. The method of claim 1, wherein the saccharide is sporadically added to the culture medium.

9. The method of claim 1, wherein the polyglutamic acid is produced in the culture medium at a concentration equal to or higher than about 25 g/L.

10. The method of claim 1, wherein the polyglutamic acid is produced in the culture medium at a concentration from about 25 g/L to about 70 g/L.

11. The method of claim 1, wherein the method is conducted in an industrial scale.

12. The method of claim 1, wherein the concentration is maintained substantially constant.

13. A method of producing polyglutamic acid while minimizing production of size-products, the method comprising:
providing a culture medium comprising a saccharide at a concentration;
culturing a microorganism of Bacillus sp. in the culture medium; and
maintaining the concentration of the saccharide not higher than about 10 g/L while sufficient to produce polyglutamic acid.

14. The method of claim 13, wherein the microorganism of Bacillus sp. is Bacillus licheniformis (ATCC 9945A).

15. The method of claim 13, wherein the saccharide is one or more selected from the group consisting of fructose, lactose, glucose, sucrose, maltose and galactose.

16. The method of claim 13, further comprising collecting polyglutamic acid at a concentration from about 25 g/L to about 70 g/L.

17. The method of claim 13, wherein the method is carried out in a batch mode except that the saccharide is added to the culture medium during the culturing.

18. The method of claim 13, wherein the saccharide is continuously added to the culture medium.

19. The method of claim 13, wherein the saccharide is sporadically added to the culture medium.

20. The method of claim 1, wherein the concentration is maintained substantially constant during the culturing.

* * * * *